United States Patent
Wolfe

(10) Patent No.: US 8,308,739 B2
(45) Date of Patent: Nov. 13, 2012

(54) MEDICAL RETRIEVAL DEVICES

(75) Inventor: Justin Wolfe, Lawrenceville, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 283 days.

(21) Appl. No.: 12/439,144

(22) PCT Filed: Aug. 28, 2007

(86) PCT No.: PCT/US2007/076984
§ 371 (c)(1),
(2), (4) Date: Feb. 26, 2009

(87) PCT Pub. No.: WO2008/070228
PCT Pub. Date: Jun. 12, 2008

(65) Prior Publication Data
US 2009/0326549 A1 Dec. 31, 2009

Related U.S. Application Data

(60) Provisional application No. 60/823,681, filed on Aug. 28, 2006.

(51) Int. Cl.
*A61B 17/22* (2006.01)
(52) U.S. Cl. .................................................... 606/127
(58) Field of Classification Search ............... 606/110, 606/113, 127, 128, 200, 159, 114
See application file for complete search history.

(56) References Cited

U.S. PATENT DOCUMENTS

| | | | | |
|---|---|---|---|---|
| 5,387,219 | A | * | 2/1995 | Rappe ............................ 606/108 |
| 5,441,044 | A | * | 8/1995 | Tovey et al. .................... 600/234 |
| 5,972,019 | A | * | 10/1999 | Engelson et al. .............. 606/200 |
| 6,368,328 | B1 | | 4/2002 | Chu et al. |
| 6,436,112 | B2 | * | 8/2002 | Wensel et al. .................. 606/159 |
| 6,551,327 | B1 | * | 4/2003 | Dhindsa ......................... 606/127 |
| 2002/0188314 | A1 | * | 12/2002 | Anderson et al. .............. 606/200 |
| 2007/0118165 | A1 | * | 5/2007 | DeMello et al. ............... 606/159 |

OTHER PUBLICATIONS

PCT/US07/76984 filed Aug. 28, 2007 International Search Report dated Aug. 15, 2008.
PCT/US07/76984 filed Aug. 28, 2007 Written Opinion dated Aug. 15, 2008.

* cited by examiner

*Primary Examiner* — Ryan Severson
*Assistant Examiner* — Jonathan W Miles
(74) *Attorney, Agent, or Firm* — Rutan & Tucker, LLP

(57) ABSTRACT

A medical retrieval device may include an elongated member having first and second end portions and a middle portion, The elongated member may be configured such that the first and second end portions are proximal one another and extend substantially parallel to one another along a longitudinal axis The middle portion may have an unconstrained basket configuration A first sheath may be configured to receive at least a portion of the first end portion, and a second sheath may be configured to receive at least a portion of the second end portion At least one of the first and second sheaths may be movable relative to the middle portion so as to constrain the middle portion in an elongated configuration.

19 Claims, 4 Drawing Sheets

MEDICAL RETRIEVAL DEVICES

PRIORITY

This application is a U.S. national stage application under 35 USC §371 of International Application No. PCT/US2007/076984, filed Aug. 28, 2007, claiming priority to U.S. Provisional Patent Application No. 60/823,681, filed Aug. 28, 2006, each of which is incorporated by reference in its entirety into this application.

The present invention relates to medical retrieval devices. More particularly, the present invention relates to medical retrieval devices and methods utilizing a retrieval device to remove stone fragments from a body lumen.

Some conventional instruments for kidney stone removal include a basket or forceps for grabbing a stone. Such instruments may be used to remove a smaller stone in one piece. However, for larger stones, a surgeon (e.g., a urologist) typically uses a laser or other instrument to first break up the larger stone into a number of fragments before attempting removal. Because of the size and/or operation of conventional baskets and forceps, the surgeon cannot remove the fragments at the same time. Instead, the surgeon typically has to remove the instrument from the patient each time a fragment is removed and then re-introduce the instrument for each additional fragment.

In addition, during the fragmentation step of a conventional ureteroscopic procedure, some fragments often migrate, for example, back toward the kidney. The migration may be due to contact with a laser fiber or as a result of pressures created during fragmentation.

It may be desirable to provide a retrieval device capable of retrieving and removing a plurality of stones and/or fragments with one removal from the body lumen. It may be desirable to provide a retrieval device capable of maintaining the position of a stone and/or fragments during a fragmentation process.

The medical retrieval devices and methods of the present invention may solve one or more of the problems set forth above.

According to various aspects of the disclosure, a medical retrieval device may include an elongated member having first and second end portions and a middle portion. The elongated member may be configured such that the first and second end portions are proximal one another and extend substantially parallel to one another along a longitudinal axis. At least one sheath may be configured to receive at least a portion of the end portions. For example, the device may comprise two sheaths, with one sheath enclosing each end portion. Alternatively, a single sheath may enclose both end portions. A handle portion may be associated with the elongated member and the sheath. The handle portion may be operable to cause relative movement between the sheath and the elongated member.

In accordance with various aspects of the disclosure, an exemplary method of removing an object from a body lumen may include positioning a medical device in a body lumen such that a distal end of the medical device is located at a desired position relative to at least one object to be removed. For example, the distal end of the medical device can be positioned distal to the object to be removed. According to various embodiments, the medical device includes a sheath and an elongated member. The method may include moving at least one of the end portions of the elongated member relative to the sheath so as to de-constrain a middle portion of the elongated member, and withdrawing the medical device from the body lumen to remove the at least one object.

DETAILED DESCRIPTION

Figure 1:
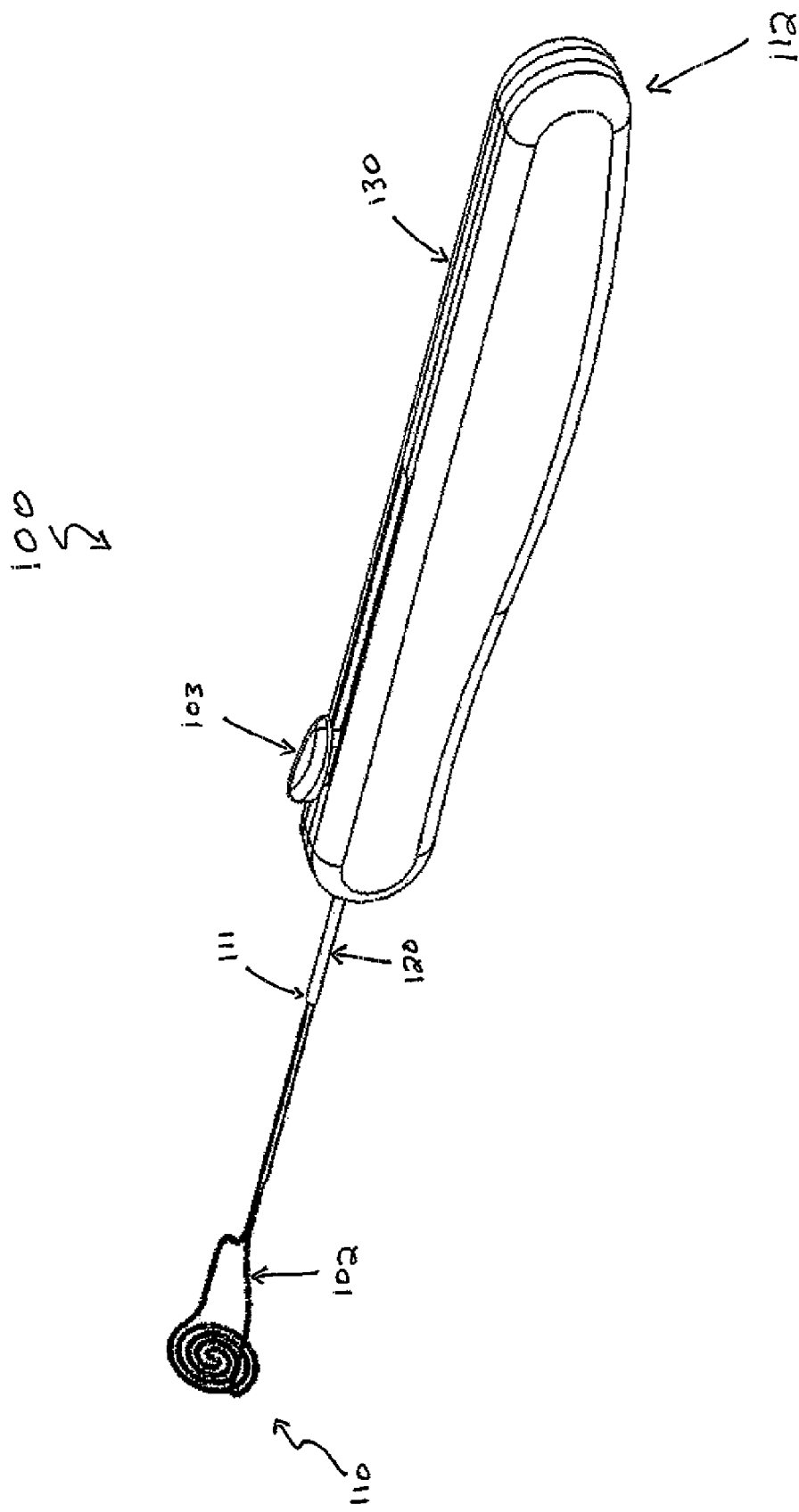
FIG. 1 is a perspective view of a medical retrieval device with an exemplary elongated member in a first configuration in accordance with exemplary aspects of the present invention.

An exemplary embodiment of a medical retrieval device 100 is illustrated in FIGS. 1-4. The medical retrieval device 100 may include an elongated member 102 having an unconstrained configuration in the shape of a basket. The medical retrieval device 100 may have a distal end 110 and a proximal end 112, a handle portion 130, and an actuating member 103. According to various embodiments, the actuating member 103 is configured to be a thumb slide.

Figure 3:
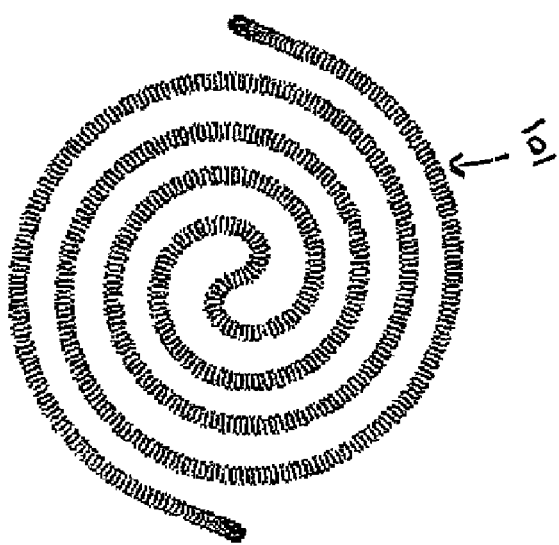
FIG. 3 is an end view of the elongated member of FIG. 2.

According to various aspects, the elongated member 102 may comprise a memory alloy such as, for example, nitinol. According to some aspects, the elongated member 102 may be a single wire or tube. According to various aspects, the elongated member 102 may comprise a laser resistant material such as, for example, a refractory metal, such as tungsten, so as to prevent the elongated member 102 from fragmenting if struck by a laser beam. According to various embodiments, and as best illustrated in FIG. 3, the elongated member 102 is encased in a flexible tungsten spring coil 101, which can prevent, or at least reduce the likelihood, of the elongated member 102 from fragmenting if struck by a laser beam.

Figure 2:
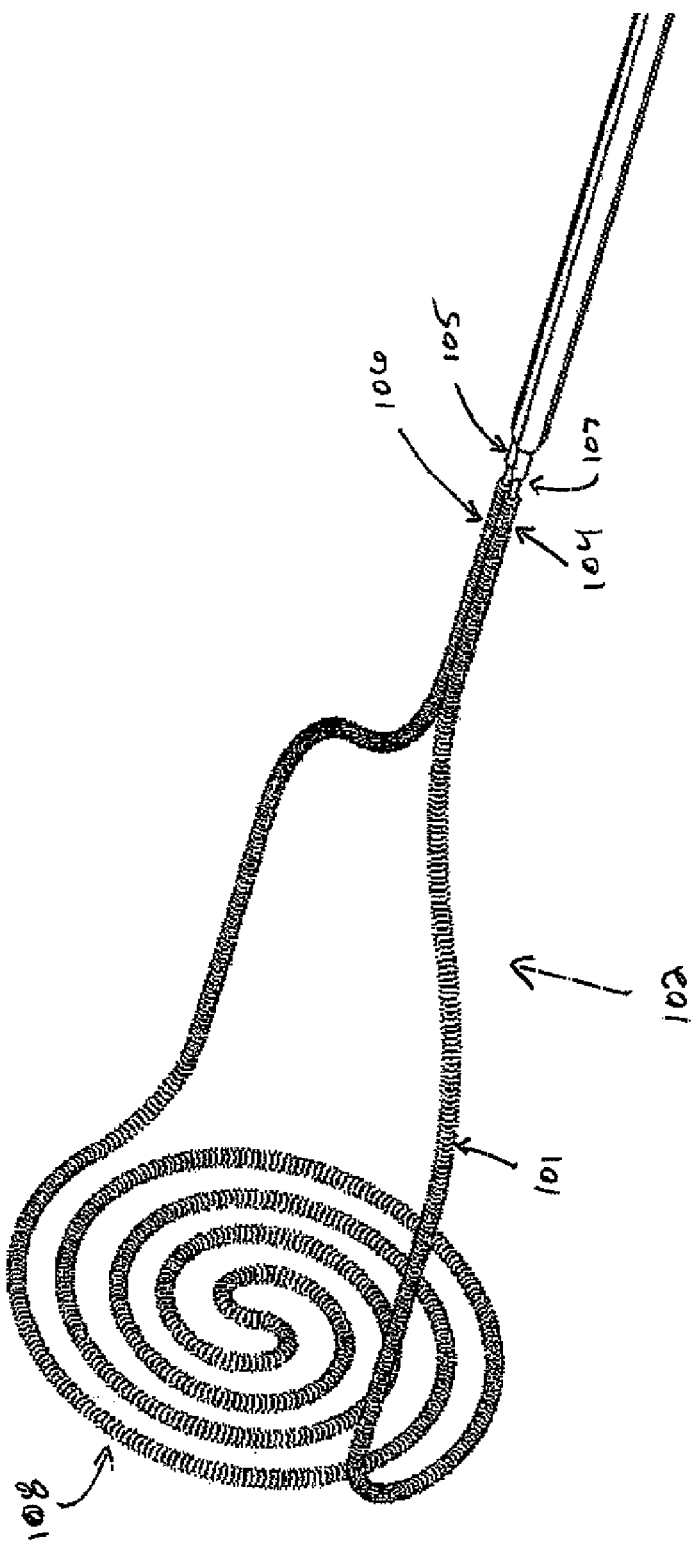
FIG. 2 is a perspective view of the elongated member of the medical retrieval device of FIG. 1.
Figure 4:
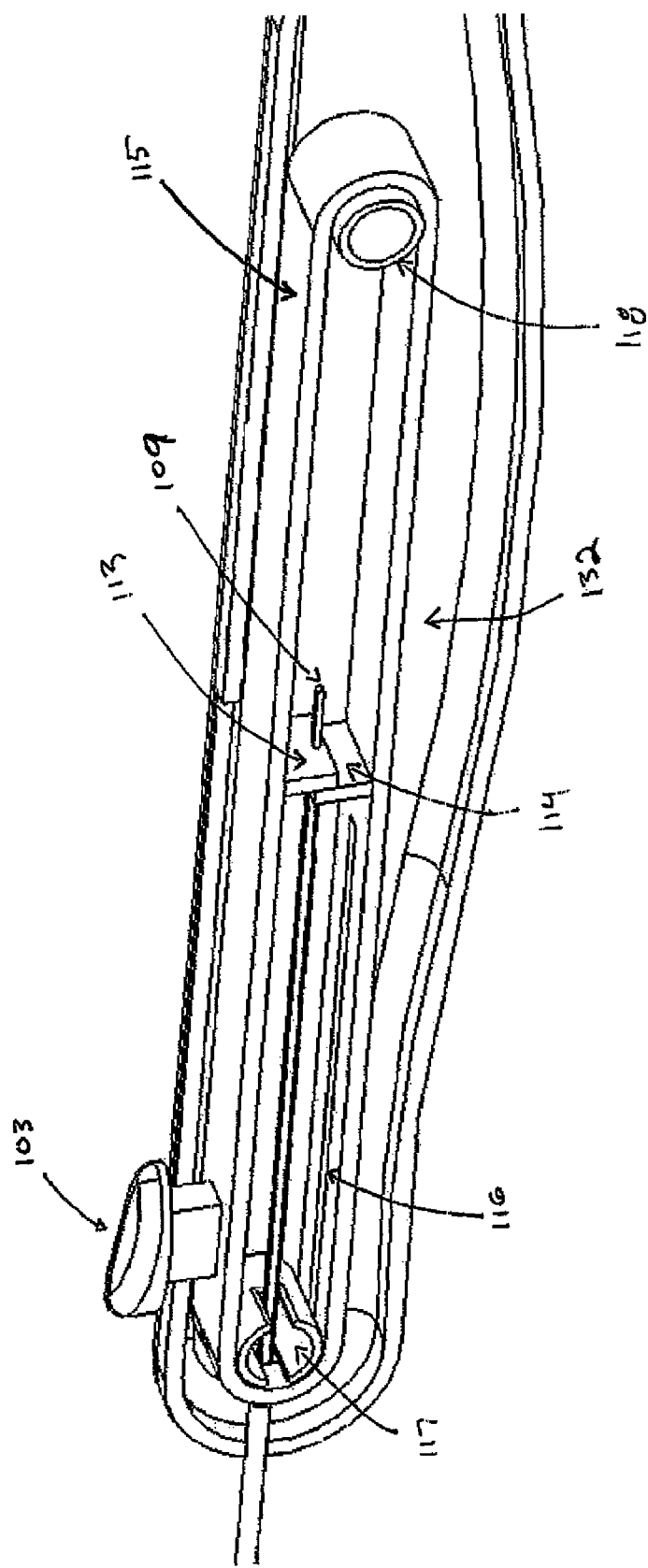
FIG. 4 is an internal view of the handle and slide mechanism of the medical retrieval device of FIG. 1.

Referring to FIG. 2, the elongated member 102 may comprise a first end portion 104, a second end portion 106, and a middle portion 108. According to various embodiments, the diameter of middle portion 108 can range from 5 to 25 mm, such as from 8 to 15 mm, for example 10 mm. End portion 102 is comprised of nitinol wire, and is wrapped by a laser-resistant tungsten coil 101. The elongated member 102 may be configured such that the first end portion 104 and second end portion 106 are proximal one another and extend substantially parallel to one another for at least a portion of their length. End portions 102 and 104 terminate in a joint 105. According to various embodiments, the joint 105 is constructed of a material other than nitinol, such as stainless steel. The termination joint has a first end 107, and a second end 109 (FIG. 4). As illustrated in FIG. 2, the middle portion 108 of the elongated wire may include a basket having a planar portion extending generally perpendicular to the longitudinal axis of, e.g., substantially parallel first and second end portions 104, 106.

The middle portion 108 of elongated member 102 may be configured as a basket when unconstrained. For example, the middle portion 108 may comprise a portion of the elongated member 102 formed into a spiral shape, a conical shape, a "strain sensor" shape, a mesh, or the like. According to various aspects, the middle portion 108 may be constrained into an elongated configuration for introduction into and placement in a body lumen, for example a ureter.

Referring again to FIG. 1, the retrieval device 100 may include at least one sheath 120. The sheath 120 has an internal diameter sufficient to enclose first and second end portions 104 and 106 of the elongated member 102 (enclosed within tungsten coil 101). The sheath 120 may comprise a lubricious coating material such as, for example, PTFE. The sheath has a first end 111, and a second end (not shown) fixed in anchor 114 (FIG. 4). According to some aspects, the sheath 120 may have an outside diameter substantially equal to 3 Fr. According to various embodiments, sheath 120 may comprise a single lumen through which the elongated member travels, or multiple lumens through which first and second ends 104 and 106 travel.

The retrieval device 102 may include a handle portion 130 proximal the sheath 120. The handle portion 130 may include one or more mechanisms configured to facilitate placement and deployment of the middle portion 108 of the elongated member 102 at a desired position in a body lumen. For examples the handle portion 130 may include an actuation mechanism 132 (FIG. 4) configured to slide the paired ends 104 and 106, and sheath 120 without relative movement to one another so that the distal end 110 of the retrieval device 100 may be at a desired position in a body lumen.

The handle portion 130 may include one or mote gears (not shown) with the actuation mechanism 132. The one or more gears may cooperate with the actuation mechanism 132 to ensure that the distal end 110 of the elongated member 102 remains substantially at the point of placement for a desired period of time without relative movement between the elongated member 102 and the body lumen.

With the distal end 110 of the elongated member 102 placed at the desired location, the actuation mechanism 132 may cooperate to deploy the elongated member 102 from the sheath 120. For example, selective operation of the actuation mechanism 132 may cause the first and second ends 104, 106 to be slide relative to the sheath 120, such that the middle portion 108 is permitted to move from the constrained configuration to the unconstrained configuration.

According to various aspects, the actuation mechanism 132 (shown in FIG. 4) may be configured such that the elongated member 102 is removed from the sheath 120 at a greater rate than that at which the sheath 120 is withdrawn relative to the desired position in the body lumen. For example, according to some aspects, the elongated member may be advanced from the distal end of the sheath 120 at a rate approximately two to three times greater than the rate at which the sheath is withdrawn proximally from the body lumen. The rate differential can be suitable because the length of wire of the middle portion 108 needed to form a basket configuration is greater than the length of wire required for positioning the device 100.

In operation, an elongated member 102 having an unconstrained configuration with a middle portion in the form of, for example, a basket, may be constrained into a substantially elongated configuration by the sheath in FIG. 2. For example, the first and second ends 104, 106 of the elongated member 102 may be withdrawn into sheath 120. In addition, at least a portion of the middle portion 108 may be withdrawn into the sheath such that a transverse dimension of the middle portion 108 is reduced to a size substantially similar to or less than a transverse dimension of the sheath 120.

Once constrained, the sheath 120 and elongated member 102 may be positioned at a desired location of a body lumen, for example, a ureter. The placement of the sheath 120 and elongated member 102 may be facilitated, for example, by the actuation mechanism 132 or other mechanical device associated with the handle portion 130. With reference to FIG. 4, actuating member 103 is attached to belt 115 having a slot 116. Anchor 113 fixes elongated member 102, and anchor 114 fixes sheath 120. Anchors 113 and 114 are each fixed to belt 115, which in turn is looped around distal cylindrical member 117 and proximal cylindrical member 118. When actuation member 103 (which may be a thumb slide) is moved in the proximal direction, the top of belt 115 moves in a proximal direction. Anchor 113, and thus elongated member 102 also move proximally, and anchor 114 and sleeve 120 move distally. Slot 116 also moves distally, allowing the elongated member 102 and sheath 120 to travel therethrough.

According to various aspects of the disclosure, a distal end of the constrained elongated member 102 may be positioned upstream (with respect to typical urine flow) of one or more kidney stones and/or fragments.

According to some aspects, for example, when the stone(s) and/or fragment(s) are sufficiently small so as not to damage the ureter during removal, the middle portion 108 of the elongated member 102 may be deployed by withdrawing the middle portion 108 from first the sheath 120, thereby allowing the middle portion 108 to achieve its unconstrained configuration, such as, for example, a basket. The sheath 120 and the elongated member 102 may then be withdrawn from the ureter and from the body, removing all stones and/or fragments along the path of withdrawal.

According to various aspects, for example, when at least one of the stone(s) and/or fragment(s) is sufficiently large that damage to the ureter during removal becomes an undesirable risk, a surgeon may first fragment the large stone(s) or fragment(s). The fragmentation may be achieved with, for example, a laser such as a holmium laser or any other laser.

Before fragmentation, the middle portion 108 of the elongated member 102 may be deployed upstream of the stone(s) and/or fragment(s) to prevent migration of fragments upstream during the fragmentation procedure Once fragmented, the sheath 120 and the elongated member 102 may then be withdrawn from the ureter and from the body, removing all stones and/or fragments along the path of withdrawal.

It will be apparent to those skilled in the art that various modifications and variations can be made in the medical retrieval devices and methods of the present invention without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A medical retrieval device, comprising:
   an elongated member having first and second end portions and a middle portion, said elongated member being configured such that said first and second end portions are proximal one another and extend substantially parallel to one another along a longitudinal axis;
   a sheath configured to receive at least a portion of the first and second end portions; and
   a handle portion separate from and associated with the elongated member and the sheath, the handle portion being operable to cause relative longitudinal movement between the handle portion, the sheath and the first and second end portions, the handle portion comprising:
      a housing enclosing a portion of the elongate member and a portion of the sheath; and
      a slide mechanism configured to simultaneously translate the sheath in a first direction and the elongate member in an opposite direction relative to the housing.

2. The device of claim 1, wherein the middle portion of the elongated member comprises a basket configuration when unconstrained.

3. The device of claim 2, wherein the handle portion is operable to move the middle portion relative to the sheath so as to constrain the middle portion into an elongated configuration.

4. The device of claim 1, wherein the handle portion includes at least one slide mechanism configured to effectuate relative movement between the elongated member and the sheath.

5. The device of claim 4, wherein the handle portion includes at least one actuating mechanism configured to maintain the middle portion of the elongated member in at least one of a desired position in a human body and a desired configuration.

6. The device of claim 1, wherein the handle portion is operable to move the middle portion of the elongated member between a constrained configuration and an unconstrained configuration by advancing the elongated member from a distal end of the sheath at a first rate and withdrawing the sheath toward the handle portion at a second rate slower than the first rate.

7. The device of claim 6, wherein the unconstrained configuration is a basket configuration and the constrained configuration is an elongated configuration.

8. The device of claim 1, wherein the elongated member comprises a shape metal wire enclosed within a refractory metal.

9. The device of claim 8, wherein the elongated member comprises nitinol.

10. The device of claim 8, wherein the refractory metal is tungsten.

11. The device of claim 1, wherein the elongated member, in its unconstrained configuration, is in a shape chosen from a spiral shape, a conical shape, a strain sensor shape, and a mesh.

12. The device according to claim 11, wherein the elongated member, in its unconstrained configuration, has a spiral shape.

13. The device according to claim 1, wherein at least one of the sheath and the elongated member has a lubricious coating thereon.

14. The device according to claim 13, wherein the lubricious coating is PTFE.

15. A medical retrieval device, comprising:
  an elongated member having a first end portion and a second end portion proximal to the first end portion and extending substantially parallel thereto along a longitudinal axis, the elongated member comprising a wire wrapped by a laser resistant coil;
  a sheath configured to receive at least a portion of both the first and second end portions; and
  a handle portion coupled to the elongated member and the sheath, the handle portion operable to cause relative movement between the sheath and the first and second end portions, the handle portion comprising:
    a housing enclosing a portion of the elongate member and a portion of the sheath; and
    a slide mechanism configured to simultaneously translate the sheath in a first direction and the elongate member in an opposite direction relative to the housing.

16. The medical retrieval device of claim 15, wherein the wire comprises nitinol and the laser resistant coil comprises tungsten.

17. The medical retrieval device of claim 15, wherein the handle portion is operable to cause movement of the sheath and the elongate element relative to the handle, the first and second end portions maintained in a coextensive parallel orientation along their respective lengths during the relative movement, the elongate member further comprising a spiral between the first and second end portions.

18. A medical retrieval device, comprising:
  an elongated member having a first end portion and a second end portion proximal to the first end portion and extending substantially parallel thereto along a longitudinal axis, a middle portion of the elongated wire including a basket extending generally perpendicular to the longitudinal axis;
  a sheath configured to receive at least a portion of the first and second end portions; and
  a handle portion separate from and associated with the elongated member and the sheath, the handle portion operable to cause relative movement between the sheath and the first and second end portions, the handle portion comprising:
    a housing enclosing a portion of the elongate member and a portion of the sheath; and
    a slide mechanism configured to simultaneously translate the sheath in a first direction and the elongate member in an opposite direction relative to the housing.

19. The medical retrieval device of claim 18, wherein the basket has a spiral shape perpendicular to the longitudinal axis.

* * * * *